(12) United States Patent
Parker et al.

(10) Patent No.: US 8,229,574 B2
(45) Date of Patent: *Jul. 24, 2012

(54) TELESCOPIC ELECTRODE ARRAY

(75) Inventors: John L. Parker, Roseville (AU); Dusan Milojevic, Wheelers Hill (AU)

(73) Assignee: Cochlear Limited, Macquarie University, NSW (AU)

(*) Notice: Subject to any disclaimer, the term of this patent is extended or adjusted under 35 U.S.C. 154(b) by 581 days.

This patent is subject to a terminal disclaimer.

(21) Appl. No.: 12/349,481

(22) Filed: Jan. 6, 2009

(65) Prior Publication Data
US 2009/0306754 A1 Dec. 10, 2009

Related U.S. Application Data

(60) Continuation-in-part of application No. 11/947,731, filed on Nov. 29, 2007, which is a division of application No. 10/785,485, filed on Feb. 23, 2004, now Pat. No. 7,328,072.

(60) Provisional application No. 61/041,185, filed on Mar. 31, 2008.

(30) Foreign Application Priority Data

Feb. 21, 2003 (AU) ................................ 2003900773

(51) Int. Cl.
*A61N 1/05* (2006.01)
(52) U.S. Cl. ......................................................... 607/137
(58) Field of Classification Search .................... 607/137
See application file for complete search history.

(56) References Cited

U.S. PATENT DOCUMENTS

| | | | |
|---|---|---|---|
| 4,261,372 A | 4/1981 | Hansen et al. | |
| 4,271,847 A * | 6/1981 | Stokes | 607/122 |
| 4,532,930 A | 8/1985 | Crosby et al. | |
| 4,574,814 A * | 3/1986 | Buffet | 607/123 |
| 5,720,099 A | 2/1998 | Parker et al. | |
| 5,800,500 A * | 9/1998 | Spelman et al. | 607/137 |
| 5,824,030 A * | 10/1998 | Yang et al. | 607/122 |
| 6,309,410 B1 | 10/2001 | Kuzma et al. | |
| 6,711,443 B2 * | 3/2004 | Osypka | 607/122 |
| 6,968,238 B1 | 11/2005 | Kuzma | |
| 6,988,007 B1 * | 1/2006 | Morgan et al. | 607/123 |
| 7,328,072 B2 * | 2/2008 | Milojevic et al. | 607/137 |
| 7,756,588 B2 * | 7/2010 | Jog et al. | 607/117 |
| 2003/0125785 A1 | 7/2003 | Kuzma et al. | |
| 2010/0191315 A1 * | 7/2010 | Bowe et al. | 607/122 |

* cited by examiner

*Primary Examiner* — Kennedy Schaetzle
(74) *Attorney, Agent, or Firm* — Kilpatrick, Townsend & Stockton, LLP.

(57) ABSTRACT

A telescoping electrode assembly and method of implantation of a telescoping electrode assembly are provided herein. The electrode assembly may comprise a plurality of telescoping sections that may, for example, be in a retracted configuration during insertion into the patient and then after insertion expanded to their final expanded configuration. These sections may have electrodes disposed therein for use in applying electrical stimulation to the patient in which the electrode is implanted.

21 Claims, 9 Drawing Sheets

TELESCOPIC ELECTRODE ARRAY

CROSS-REFERENCE TO RELATED APPLICATIONS

The present application claims the benefit of U.S. Provisional Patent Application 61/041,185; filed Mar. 31, 2008, which is hereby incorporated by reference herein. This application is a continuation-in-part of U.S. patent application Ser. No. 11/947,731, filed Nov. 29, 2007, which is a divisional application of U.S. patent application Ser. No. 10/785,485 filed on Feb. 23, 2004 (now U.S. Pat. No. 7,328,072) which claims priority of Australian Patent application No. 2003900773, filed Feb. 21, 2003, all of which are hereby incorporated by reference herein.

BACKGROUND

1. Field of the Invention

The present invention relates to an implantable device and, in particular, to a tissue-stimulating device.

2. Related Art

Hearing loss, which may be due to many different causes, is generally of two types, conductive and sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often addressed with conventional hearing aids which amplify sound so that acoustic information can reach the cochlea.

In many people who are profoundly deaf, however, the reason for their deafness is sensorineural hearing loss. Sensorineural hearing loss occurs when there is damage to the inner ear or to the nerve pathways from the inner ear to the brain. Those suffering from sensorineural hearing loss are thus unable to derive suitable benefit from conventional hearing aids. As a result, hearing prostheses that deliver electrical stimulation to nerve cells of the recipient's auditory system have been developed to provide persons having sensorineural hearing loss with the ability to perceive sound. Such stimulating hearing prostheses include, for example, auditory brain stimulators and Cochlear™ prostheses (commonly referred to as Cochlear™ prosthetic devices, Cochlear™ implants, Cochlear™ devices, and the like; simply "cochlea implants" herein.) As used herein, the recipient's auditory system includes all sensory system components used to perceive a sound signal, such as hearing sensation receptors, neural pathways, including the auditory nerve and spiral ganglion, and parts of the brain used to sense sounds.

Most sensorineural hearing loss is due to the absence or destruction of the cochlea hair cells which transduce acoustic signals into nerve impulses. It is for this purpose that cochlear implants have been developed. Cochlear implants use direct electrical stimulation of auditory nerve cells to bypass absent or defective hair cells that normally transduce acoustic vibrations into neural activity. Such devices generally use an electrode array implanted into the scala tympani of the cochlea so that the electrodes may differentially activate auditory neurons that normally encode differential pitches of sound.

Auditory brain stimulators are used to treat a smaller number of recipients with bilateral degeneration of the auditory nerve. For such recipients, the auditory brain stimulator provides stimulation of the cochlear nucleus in the brainstem.

SUMMARY

In one aspect of the present invention, an elongate electrode assembly for a cochlear implant having a proximal end and a distal end is provided. The elongate electrode assembly comprises a base at the proximal end, a tip at the distal end, one or more telescoping sections between the base and the tip, and a plurality of electrodes disposed on any one or more of the base, tip and telescoping sections, wherein adjacent telescoping sections are slidably engaged with one another and movable between a retracted configuration and an expanded configuration.

In another aspect, cochlear electrode assembly kit is disclosed. The kit comprises an elongate electrode assembly for a cochlear implant having a proximal end and a distal end. The elongate electrode assembly comprises a base at the proximal end, a tip at the distal end, one or more telescoping sections between the base and the tip, and a plurality of electrodes disposed on any one or more of the base, tip and telescoping sections, wherein adjacent telescoping sections are slidably engaged with one another and movable between a retracted configuration and an expanded configuration, and wherein the plurality of telescoping sections and the tip define a lumen. The kit also comprises a stylet configured to fit into the lumen and extend substantially through the telescoping sections to deploy the elongate electrode assembly from the retracted configuration to the expanded configuration.

In yet another aspect, there is provided a method for implantation of a telescoping cochlear electrode assembly, wherein the electrode assembly comprises: a base at the proximal end, a tip at the distal end, one or more telescoping sections between the base and the tip, and a plurality of electrodes disposed on any one or more of the base, tip and telescoping sections, wherein adjacent telescoping sections are slidably engaged with one another and movable between a retracted configuration and an expanded configuration. This method comprises inserting the electrode assembly in its retracted configuration into a base of a patients cochlea, and expanding the electrode assembly to the expanded configuration.

BRIEF DESCRIPTION OF THE DRAWINGS

Illustrative embodiments of the present invention are described herein with reference to the accompanying drawings, in which.

DETAILED DESCRIPTION

Embodiments of the present invention are generally directed to an apparatus and method for an electrode assembly for use in tissue-stimulating prosthesis. In an embodiment, the electrode assembly comprises a plurality of telescoping sections that may, for example, be in a retracted configuration during insertion into the patient and then after insertion expanded to their final expanded configuration.

Embodiments of the present invention are described herein primarily in connection with one type of hearing prosthesis, namely a Cochlear™ prostheses (commonly referred to as Cochlear™ prosthetic devices, Cochlear™ implants, Cochlear™ devices, and the like; simply "cochlea implants" herein.) Cochlear implants generally refer to hearing prostheses that deliver electrical stimulation to the cochlear of a recipient. As used herein, cochlear implants also include hearing prostheses that deliver electrical stimulation in combination with other types of stimulation, such as acoustic or mechanical stimulation. It would be appreciated that embodiments of the present invention may be implemented in any cochlear implant or other hearing prosthesis now know or later developed, including auditory brain stimulators, or implantable hearing prostheses that acoustically or mechanically stimulate components of the recipient's middle or inner ear.

Figure 1:
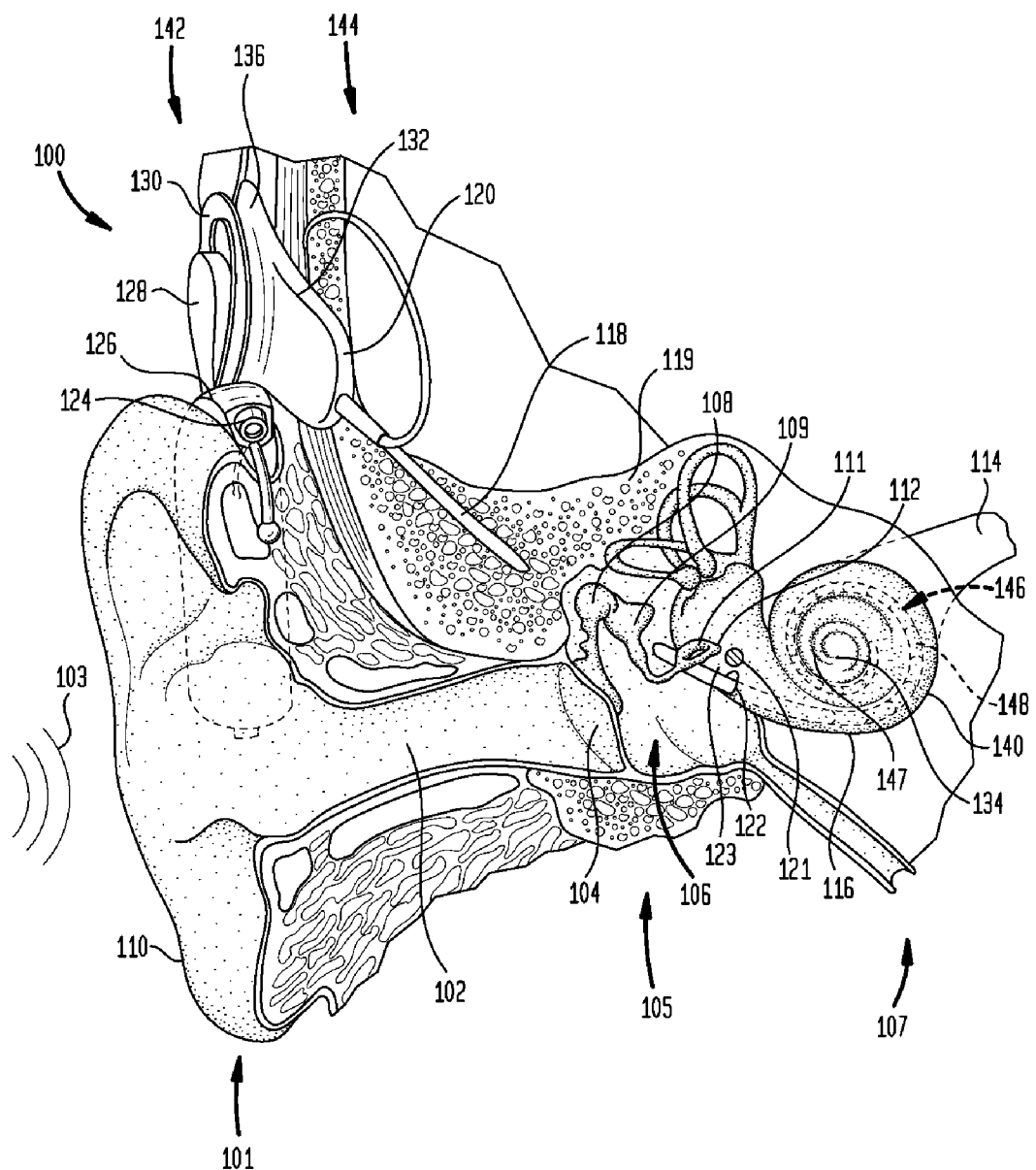
FIG. 1 is a perspective view of a cochlear implant in which embodiments of the present invention may be implemented.

FIG. 1 is perspective view of a conventional cochlear implant, referred to as cochlear implant 100 implanted in a recipient having an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processing unit 126, a power source (not shown), and an external transmitter unit 128. External transmitter unit 128 comprises an external coil 130 and, preferably, a magnet (not shown) secured directly or indirectly to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown).

Internal component 144 comprises an internal receiver unit 132, a stimulator unit 120, and an elongate electrode assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives power and stimulation data from external coil 130, as noted above. Elongate electrode assembly 118 has a proximal end connected to stimulator unit 120, and a distal end implanted in cochlea 140. Electrode assembly 118 extends from stimulator unit 120 to cochlea 140 through mastoid bone 119. Electrode assembly 118 is implanted into cochlea 104. As described below, electrode assembly is implanted in cochlea 140. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, sometimes referred to as electrode array 146 herein, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals which are applied by electrodes 148 to cochlea 140, thereby stimulating auditory nerve 114. As will be discussed in more detail below, in accordance with an embodiment, electrode assembly 118 may be comprised of a plurality of telescoping sections that may be collapsed during implantation and then expanded to its elongated state as illustrated in FIG. 1 The electrodes of the electrode array 146 may be disposed in each of these sections. A further description of exemplary electrode assemblies comprising telescoping sections is provided below, as well as exemplary methods for their implantation.

In cochlear implant 100, external coil 130 transmits electrical signals (i.e., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

Figure 2A:
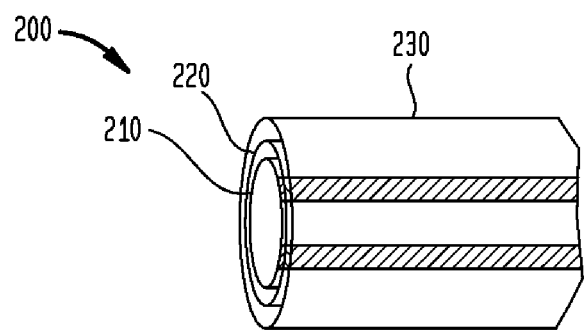
FIGS. 2A-B are partial perspective views of telescoping sections of an electrode assembly in a collapsed state and an expanded state, respectively, in accordance with an aspect of the invention.
Figure 2B:
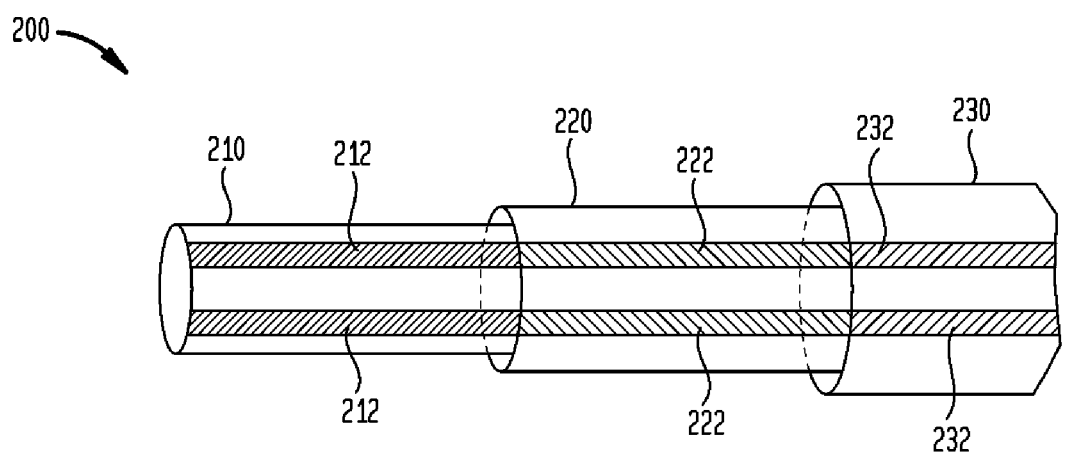

FIGS. 2A-B provide partial views of a telescoping electrode assembly 200 comprising a plurality of telescoping sections 210, 220, 230 nested together in a retracted state (FIG. 2A) and expanded in a deployed state (FIG. 2B). This electrode assembly 200 may be used as electrode assembly 118 of FIG. 1. As used herein, the term "nested" refers broadly to a section to be located in its retracted state regardless of whether the section is a cylindrical, rectangular, or any other shape. For example, if the sections are rectangular in shape with one section located on top of the other, the sections will be considered nested if they are in there retracted state.

The plurality of telescoping sections 210, 220, 230, as illustrated, each comprise a pair of electrodes 212, 222, 232 spaced radially along the outer surface of the telescoping sections 210, 220, 230. The telescoping sections 210, 220, 230 have increasing cross-sectional diameters, such that each telescoping section nests within an adjacent larger telescoping section. As used herein, the term "telescoping sections" refers to sections that can slide inward or outward with respect to each other. Although the telescoping sections 210, 220, and 230 are illustrated as being cylindrical in shape, it should be understood that in other embodiments the telescoping sections (and resulting electrode assembly) may have different shapes, such as, for example, rectangular, triangular, etc. Additionally, the outermost telescoping section 210 is referred to herein as the tip 210. And, innermost telescoping section (not shown) will be referred to as the base. In cochlear implant systems, the base of the assembly may be the section closest to the stimulating unit.

While the radially-spaced electrodes 212, 222, 232 appear to be longitudinally continuous, electrodes of adjacent sections 210, 220, 230 are electrically discontinuous. Thus, the electrode assembly is capable of delivering electrical stimulation in any one or a combination of radial mode, longitudinal mode, and radial-longitudinal mode. The electrodes in adjacent sections may be longitudinally spaced apart to provide electrical discontinuity. Electrode assemblies comprising radial and/or longitudinal spaced electrodes are disclosed in more detail in the co-pending U.S. Patent Application by John Parker entitled "Electrode Assembly for Delivering Longitudinal and Radial Stimulation", filed concurrent with the present application, the contents of which are incorporated herein by reference.

Figure 3A:
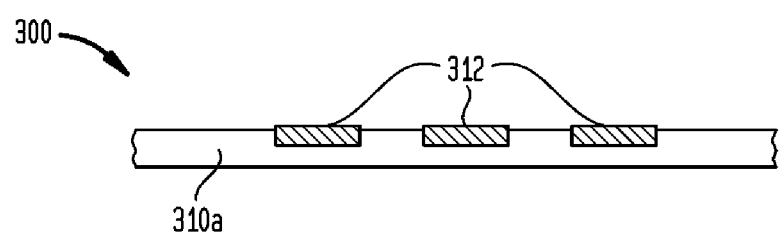
FIG. 3A-B illustrate a method of making a telescoping section of a telescoping electrode assembly, in accordance with an aspect of the present invention.
Figure 3B:
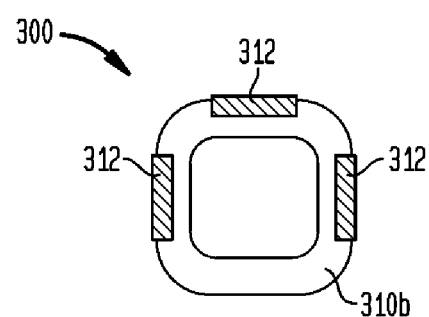

FIGS. 3A-B show one method of making a telescoping section in accordance with the embodiments disclosed herein. As shown in FIG. 3A, the telescoping section 300 may be configured from a substantially flat, planar carrier material 310a having a plurality of electrodes 312 disposed thereon. The planar carrier material may be formed of a biocompatible material, such as polyurethane, silicone, a flexible silicone elastomer or a similar material. Silastic MDX 4-4210 is an example of one suitable silicone elastomer for use in the formation of the carrier member. The electrodes may be formed by any number of methods, including those disclosed in commonly-owned U.S. Pat. No. 7,240,416, which is incorporated herein by reference. In the embodiment depicted in FIG. 3A, the planar carrier material comprises three electrodes 312 spaced apart.

The planar carrier material 310a may be formed into a tubular structure 310b by joining opposing ends together. Because each telescoping section is configured to nest within larger telescoping sections, the diameters of the telescoping sections may be configured to be large enough to accommodate and house the smaller adjacent telescoping sections. This may be done simply by controlling the dimensions, such as the width, of the planar carrier material 310a, since this width will roughly correspond to the circumference (C), and thus of the diameter (d=C/π) of the formed tubular structure.

Figure 4A:
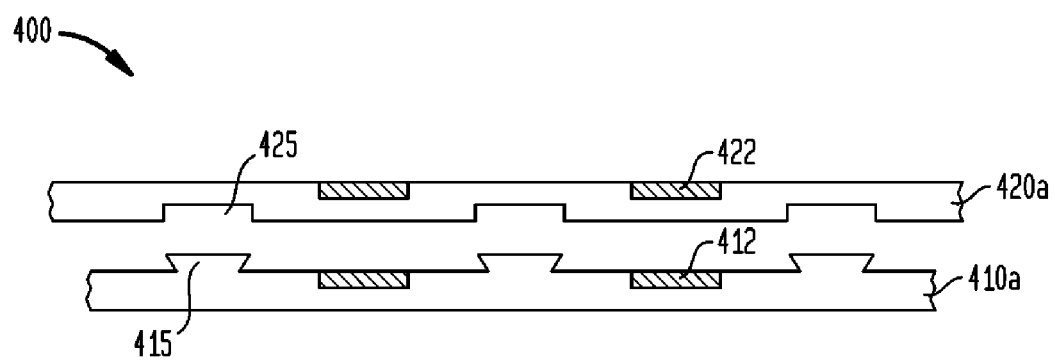
FIGS. 4A-B illustrate another method of making and assembling telescoping sections of a telescoping electrode assembly, in accordance with an aspect of the present invention.
Figure 4B:
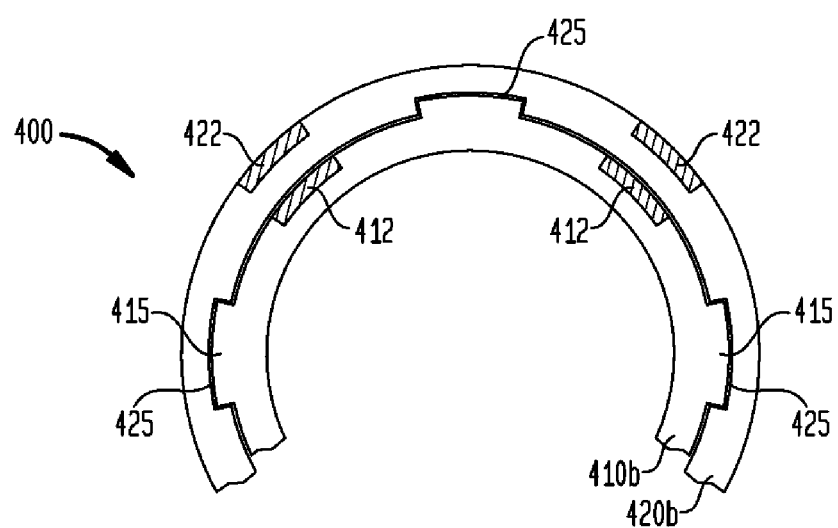

FIGS. 4A-B provide a cross-section view of another mechanism for providing a telescoping electrode assembly. As illustrated electrode assembly 400 may be constructed from a plurality of layers 410a, 420a which are formed into concentric semi-tubular structures 410b, 420b. FIG. 4A depicts two planar carriers 410a, 420a comprising a pair of electrodes 412, 422 disposed thereon. The width of planar carrier 410a is smaller than the width of planar carrier 420a such that the semi-tubular structure 410a will nest within the larger semi-tubular structure 320b. Moreover, the length of each telescoping sections may be manipulated so as to control the number of telescoping sections required to create an elongate electrode array of a desired length. In an embodiment, the lengths of the telescoping sections are roughly equal. In another embodiment, the lengths of the telescoping sections are different (e.g., decreasing length with decreasing width). While FIGS. 4A and 4B depict only two telescoping sections, it is understood that the method may be repeated with additional planar carriers to create an elongate electrode assembly of a desired length.

FIGS. 4A-B further depict a mating locking mechanism comprising rails 415 and recesses 425 formed on adjacent telescoping sections 410, 420. The locking mechanism is configured to prevent adjacent telescoping section from rotating relative to one another. Because the electrodes 412, 422 are typically implanted to face the cochlear wall, the locking mechanism may be used to help keep the telescoping sections in the same orientation such that they do not rotate relative to one another. As illustrated, rails 415 protrude from an outer surface and extend longitudinally along telescoping section 410. The rails 415 may be mated with corresponding recesses 425 disposed in an inner surface of an adjacent and larger telescoping section 420. A locking mechanism, such as the one depicted in FIGS. 4A-B, may be provided in some or all of the telescoping sections of the elongate electrode assembly. The locking mechanism functions to prevent adjacent telescoping sections from rotating relative to one another and to allow adjacent telescoping sections to slide relative to one another between a nested and deployed state.

In addition to maintaining the desired orientation of the electrodes on the telescoping electrode assembly 400, the locking mechanism may also be configured to space adjacent telescoping sections apart. This may reduce or prevent friction between the electrodes and the inner surfaces of the adjacent telescoping sections when the telescoping sections are actuated between a nested retracted state and a deployed state. Thus, in an embodiment, the rails are configured to have a height that is greater than the depth of the corresponding recess. Further, although FIGS. 4A-B illustrate semi-tubular telescoping sections, in other embodiments the sections may have different shapes. For example, the exemplary locking mechanism of FIGS. 4A-B may be used with tubular shaped telescoping sections such as discussed above with reference to FIGS. 3A-B.

In accordance with another embodiment, friction between adjacent telescoping sections may be reduced or prevented by patterning the inner and/or outer surfaces of the telescoping sections to minimize the contact area. In one embodiment, the pattern may comprise a series of ridges and/or grooves. In another embodiment, the ridges may be formed by a number of separate guidewires extending longitudinally and positioned between the inner surface of one telescoping section and the outer surface of another adjacent telescoping section. Still further, one or more guidewires may extend spirally through the telescoping sections and be positioned between the respective surfaces.

In addition to, or in place of, configuring the telescoping sections to reduce friction, the outer and/or inner surfaces of the telescoping sections may also be coated with a lubricious material. The lubricious material may become lubricious on being brought into contact with a fluid, such as a saline solution. Still further, the coating may become lubricious on being brought into contact with a bodily fluid, such as cochlear fluid. In one embodiment, the lubricious material is selected from the group consisting of polyacrylic acid (PAA), polyvinyl alcohol (PVA), polylactic acid (PLA), polyglycolic acid (PGA), and other similar materials.

As noted above, in embodiments the disclosed electrode assembly may be implanted into the cochlea of a patient suffering from hearing loss. In such embodiment, the electrode assembly may be sized and adapted for insertion through a cochleostomy and into the scala tympani of the cochlea of the patient when the telescoping electrode assembly is in a retracted state, i.e., nested within the base. Following insertion of the telescoping electrode assembly, the tip and the other telescoping sections may be moved forwardly out of the distal end of the base. This movement results in the tip and the telescoping sections travelling further into the patient's cochlea and ultimately to its fully deployed and implanted state.

Figure 5A:
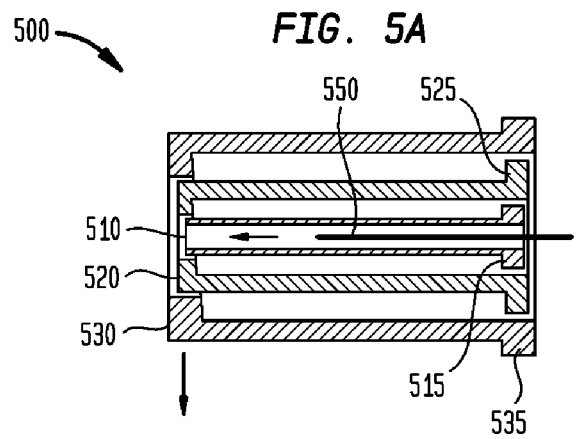
FIGS. 5A-C illustrate a method of deploying an embodiment of a telescoping electrode assembly, in accordance with an aspect of the present invention.
Figure 5B:
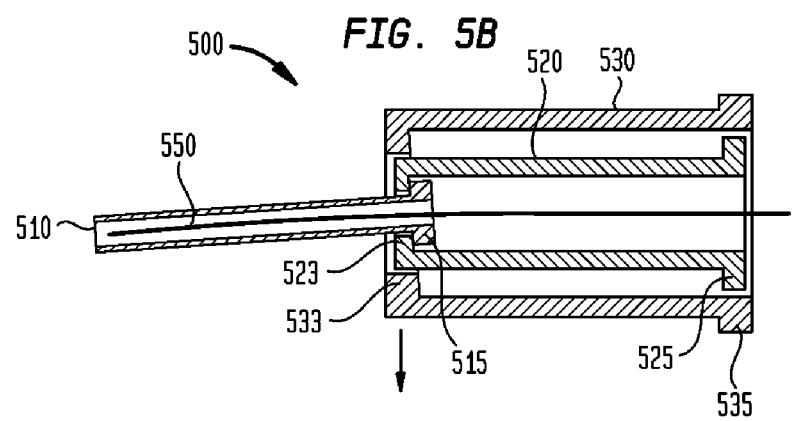
Figure 5C:
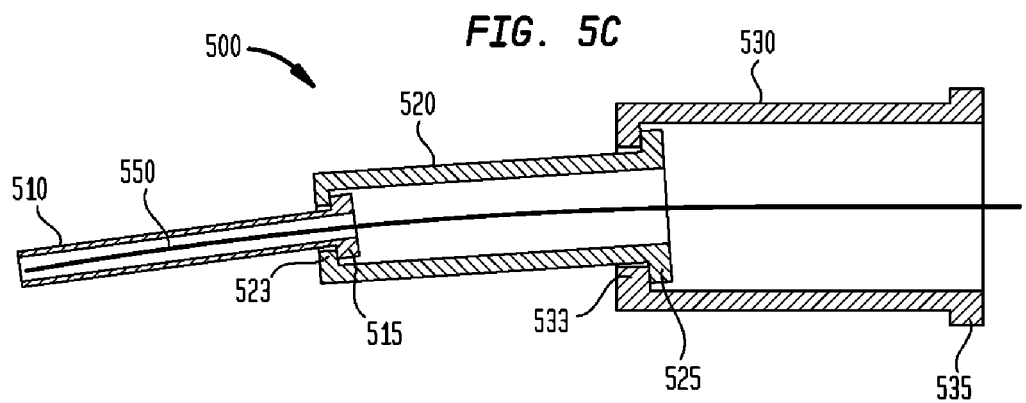

FIGS. 5A-C illustrate an exemplary method of deploying a telescoping electrode assembly in which the telescoping sections are deployed out of the nested configuration one section at a time. FIG. 5A shows the telescoping electrode assembly 500 in a retracted state in which the tip 510 and telescoping sections 520, 530 are nested. The telescoping electrode assembly may be deployed in an expanded state by inserting a stylet 550 into the lumen defined by the telescoping sections 510, 520, 530. As noted above, the smallest telescoping section 510 is referred to as the tip 510. The stylet 550 is advanced in a forward direction and to deploy the tip 510 first. Once the tip 510 is fully deployed (FIG. 5B), the adjacent telescoping section 520 is deployed (FIG. 5C). Each adjacent telescoping section is fully deployed before the next telescoping section is deployed. This manner of deploying the telescoping electrode assembly 500 may be suitable in instances where it is desirable to implant less than the entire length of the electrode array. This affords greater flexibility in adjusting the length of the electrode array that is desired to be implanted in the recipient.

As shown in FIGS. 5A-C, the telescoping electrode assembly may further comprise a plurality of stops to prevent the tip 510, telescoping sections 520, 530 and base (not shown) from disengaging from one another. In the embodiment depicted in FIGS. 5A-C, the stops comprise outer flanges 515, 525, 535 disposed at the proximal ends of the tip 510 and telescoping sections 520, 530, respectively. The outer flanges 515, 525 are configured to abut inner flanges 523, 533 disposed in the lumen of the telescoping sections 520, 530. As shown in FIGS. 5A-C, the outer flanges 515, 525 abut the inner flanges 523, 533 to prevent the tip 510 and telescoping section 520 from disengaging. In the embodiment depicted in FIGS. 5A-C, inner flanges 523, 533 are disposed at the distal ends and extends inwardly into the lumen of the telescoping sections 520, 530. In an embodiment, the materials and diameters of the electrode assembly 500 may be such that the friction does not result in the sections simultaneously deploying; rather, a section may slide out to its furthest deployed section before the next section begins deployment. In such an example, once a section reaches its furthest deployed position, the stops and flanges for the section and the next section, respectively, engage and exert a force on the next telescoping section that causes it to begin deploying.

In another embodiment, the tip and telescoping sections may be prevented from disengaging by configuring the lumens of the telescoping sections with a lumen having a cross-sectional diameter that decreases from the proximal to distal ends. Thus, for example, the cross-sectional diameter of the proximal end of a given telescoping section is configured to be greater than the cross-sectional diameter of its distal end. In this way, the telescoping sections are free to be deployed until frictional engagement between the telescoping sections prevents further deployment. This increase in frictional engagement may be such that it can be felt by the surgeon implanting the device and thus alert the surgeon to the probability that maximum insertion depth of the telescoping electrode assembly has been reached.

Figure 6A:
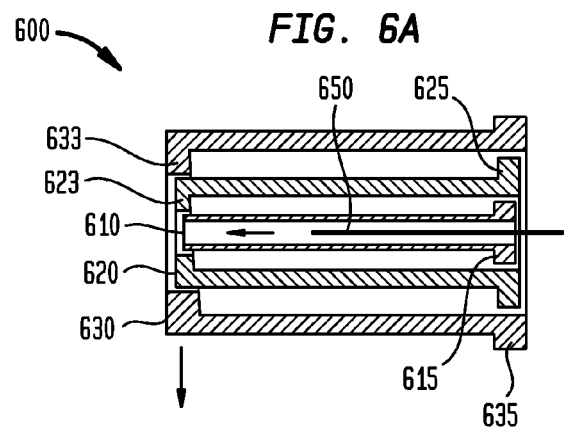
FIGS. 6A-C illustrate another method of deploying an embodiment of a telescoping electrode assembly, in accordance with an aspect of the present invention.
Figure 6B:
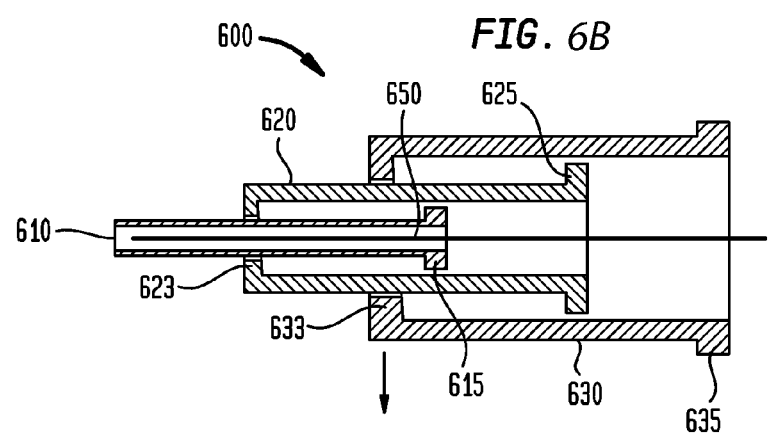
Figure 6C:
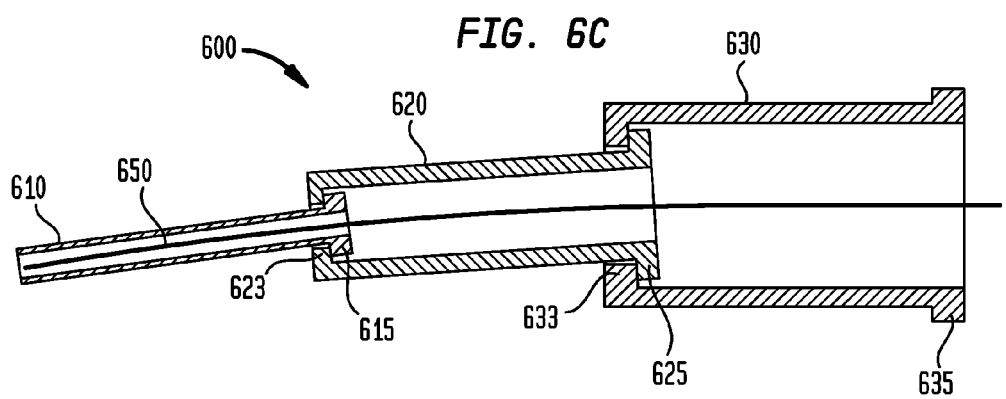

FIGS. 6A-C illustrate another method of deploying a telescoping electrode assembly 600 in which the telescoping sections 610, 620, 530 are deployed simultaneously. FIG. 6A shows a portion of the distal end of the telescoping electrode assembly 600 in a retracted state. As shown in FIGS. 6B and 6C, as the stylet 650 is advanced forward through the lumen of the electrode assembly 600, it urges the telescoping sections 610, 620, 630 out of the nested configuration. The diameters and/or materials of the telescoping sections 610, 620, 630 may be such that friction between the sections during deployment causes the sections 610, 620, 630 to simultaneously deploy. For example, the diameters of telescoping sections may be such that neighboring sections are in at least partial contact with each other circumferentially around the diameter of the sections such that during deployment sufficient friction is generated between the sections so that the sections simultaneously deploy.

The telescoping electrode assembly 600 may also be configured with a plurality of stops to prevent the telescoping sections 610, 620, 630 and base (not shown) from disengaging from one another. As illustrated in FIGS. 6A-C, the stops comprise outer flanges 615, 625, 635 on the outer surface and inner flanges 623, 633 on an adjacent inner surface of the telescoping sections. As described with reference to FIGS. 5A-C, the outer flanges 615, 625 are configured to abut the inner flanges 623, 633 disposed in the inner surface of the telescoping sections to prevent disengagement.

Figure 7:
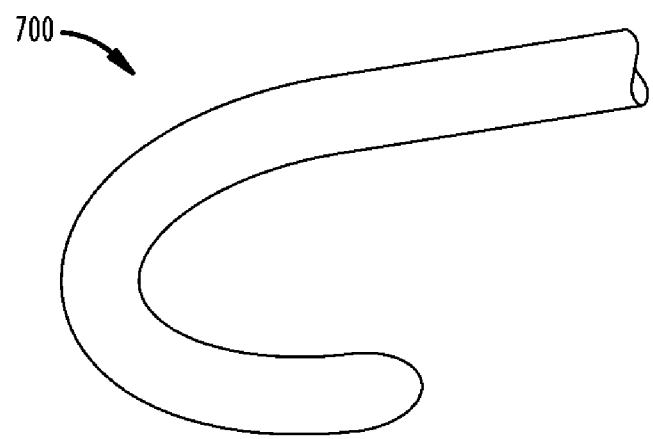
FIG. 7 is a perspective view of a pre-curved stylet, in accordance with an aspect of the present invention.

FIG. 7 illustrates an exemplary stylet 700 that may be used in connection with the telescoping electrode assemblies disclosed herein. As illustrated, exemplary stylet 700 is pre-curved in a shape that approximates the curvature of the modiolar wall of the cochlea. Stylet 700 may be used for deploying the electrode assemblies in a manner, such as, for example, as discussed above with references to FIGS. 5-6.

In an embodiment, the stylet is initially inserted into the lumen of the telescoping electrode assembly in a collapsed configuration just prior to implantation. Thus, the stylet will assume a straight shape as the thickness of the nested telescoping sections prevents the stylet from taking on its pre-curved configuration. As the stylet is advanced through the lumen of the assembly and deploys the telescoping sections, the forces that keep the stylet straight gradually decrease, thereby allowing the stylet to resume its pre-curved shape and urge the telescoping sections accordingly. For example, in embodiments where the tip and telescoping sections are simultaneously deployed, as depicted in FIGS. 6A-C, the forces that keep the stylet straight decrease as the stylet is advanced through the lumen to deploy the assembly. Once the assembly is fully deployed, the stylet is able to return substantially to its pre-curved shape to urge the assembly close to the modiolar wall of the cochlea.

Figure 8A:
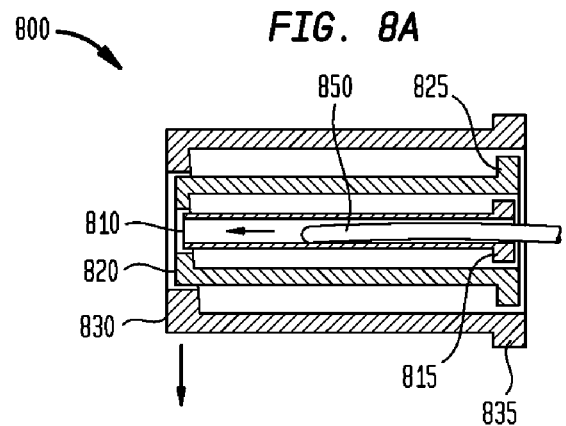
FIGS. 8A-C illustrate a further embodiment of a telescoping electrode assembly in various stages of deployment using a pre-curved stylet, in accordance with an aspect of the present invention.
Figure 8B:
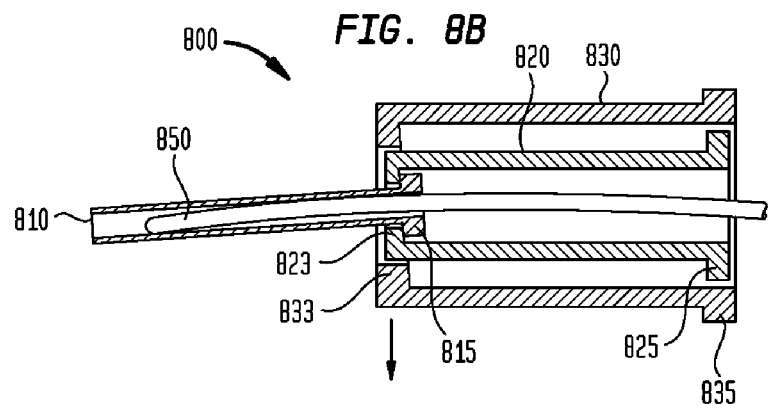
Figure 8C:
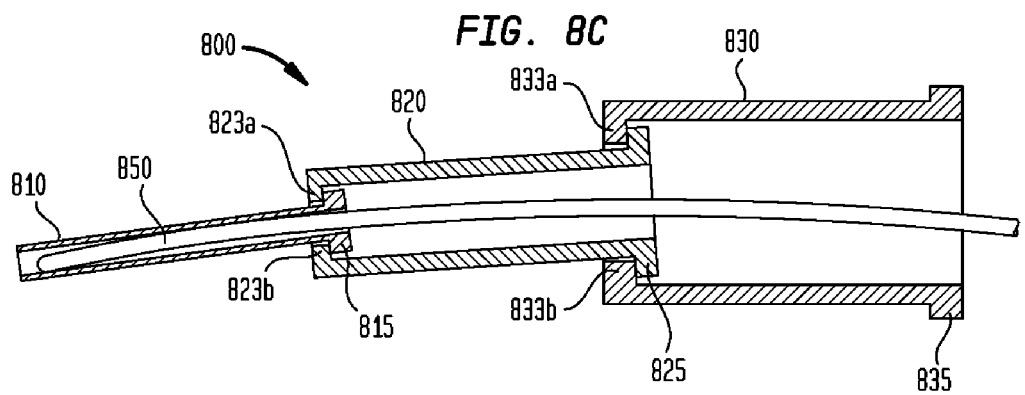

FIGS. 8A-C illustrate another embodiment of a telescoping electrode assembly 800 in various stages of deployment using a pre-curved stylet 850, such as the one depicted in FIG. 7. FIG. 8A shows the telescoping electrode assembly 800 in a retracted configuration in which the telescoping sections 810, 820, 830 are nested. In this retracted configuration, the telescoping sections 810, 820, 830 keep the pre-curved stylet 850 in a substantially straight shape. As shown in FIG. 8B, as the pre-curved stylet 850 advances the tip 810 (i.e., the smallest diameter section) out of the nested sections 820, 830, the forces that keep the stylet 850 straight is substantially decreased and the tip 810 begins to take on the curved configuration corresponding to the pre-curved stylet 850. As the adjacent telescoping section 820 is subsequently deployed (FIG. 8C), the telescoping electrode assembly 800 increasingly begins to assume the pre-curved shape corresponding to that of the stylet 850. In an embodiment, the material for the tip 810 in which the electrodes are disposed may be manufactured from a different material than the other sections. This material for tip 810 may be, for example, a more flexible material that may help in curving the tip to fit the more inner portion of the cochlea. Similarly, in other embodiments, each of the sections of the electrode assembly may be made from the same or different materials with the electrodes disposed therein.

The telescoping electrode assembly 800 may also be configured to take on a curved shape upon deployment. Such a telescoping assembly 800 may be used with or without a pre-curved stylet 850. As illustrated, telescoping electrode assembly 800 comprises a series of internal abutments 823a, b and 833a, b disposed within the lumen of the telescoping sections 820, 830 that help urge the each subsequent telescoping section to deploy in a similar manner as was discussed above with reference to FIG. 5. As shown in FIG. 8C, the outer surface of the tip 810 is provided with a stop 815 which meets with internal abutment 823a, b of the telescoping section 820 within which it is nested. Similarly, the outer surface of the telescoping section 820 is provided with a stop 825 which meets with internal abutments 833a, b.

The internal abutments 823a, b may be configured as a single peripheral rim that surrounds the distal opening of the telescoping section 820 being narrower along the top portion 23a and a wider along the bottom portion 823b. Alternatively, the internal abutments 823a, b and 833a, b may also be provided as two separate structures, in which the top abutments 823a, 833a have narrower widths than the lower abutments 823b, 833b.

As shown in FIGS. 8A-C, the configuration of the internal abutments 823a, b and 833a, b biases the tip 810 and the telescoping section 820, respectively, in a curved shape. Thus, as each subsequent telescoping section is deployed, the array may take on an increasingly curved configuration. The degree of curvature of the deployed array may be manipulated by the shape of the internal abutments. In the embodiment depicted in FIGS. 8A-C, the degree of curvature for the telescoping electrode assembly 800 may be increased by providing a greater differential between the widths of the abutments 823a, b and 833a, b. Thus, the greater the difference in width between the abutments 823a, b, for example, the greater the curvature provided between the tip 810 and adjacent telescoping section 820. In an embodiment, the internal abutments of the telescoping sections may vary so as to provide varying degrees of curvature. For example, it may be desirable to increase the degree of curvature from the proximal to the distal portion of the telescoping electrode assembly. Thus, the telescoping sections may be provided with abutments having increasing differentials in width.

Alternatively, the telescoping electrode assembly 800 may be configured to be curved in a deployed state by configuring the stops 815, 825 provided at the proximal ends of the tip 810 and telescoping sections 825. In this embodiment, the abutment 823a, b and 833a, b may be a rim having uniform dimensions along its periphery with the stops 815, 825 having the narrowed and wider portions. As with the embodiment depicted in FIGS. 8A-C, this will result in biasing adjacent telescoping sections at various angles, depending on the configuration of the stops (i.e., the differential in width).

Figure 9A:
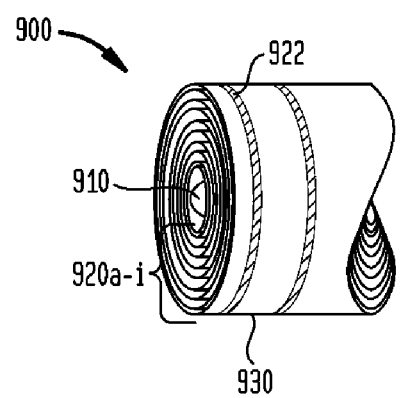
FIGS. 9A-B are perspective views of an embodiment of a telescoping electrode assembly in a collapsed state and an expanded state, respectively, in accordance with an aspect of the present invention.
Figure 9B:
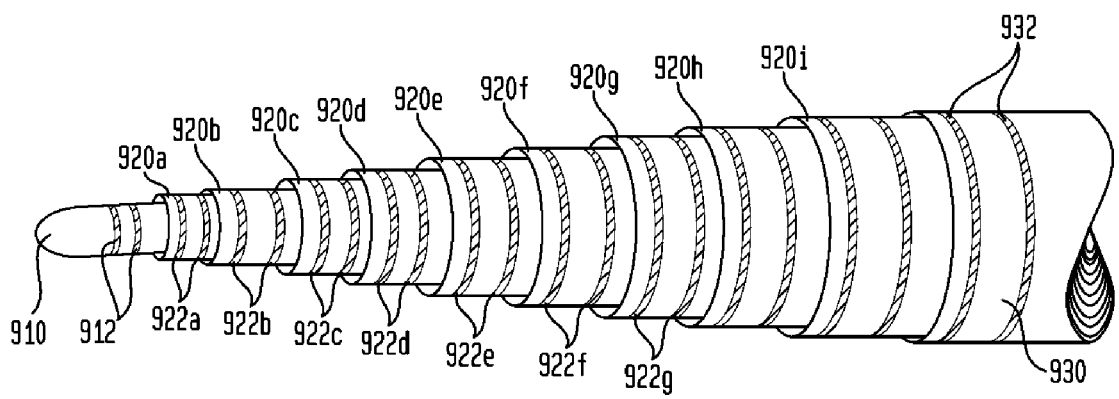

FIGS. 9A-B are perspective views of an embodiment of the telescoping electrode assembly in a collapsed state and an expanded state, respectively. Because the telescoping electrode assembly 900 is assumes a substantially straight configuration upon deployment, it is particularly suited for use with the pre-curved stylet depicted and described in connection with FIG. 7. Thus, the telescoping electrode assembly 900 may be constructed from materials which are readily malleable or deformable into a desired shape. The telescoping electrode assembly 900 generally comprises a tip 910, a plurality of telescoping sections 920a-i, and a base 930 within which the tip 910 and telescoping sections 920a-i may nest prior to deployment.

In the embodiment depicted in FIGS. 9A-B, the telescoping electrode assembly 900 comprises a total of 22 electrodes (912, 922a-i, 932), with two longitudinally-spaced electrodes disposed at each one of the tip 910, the telescoping sections 920a-i and the base 930. It is understood that any number of electrodes may be disposed on any one or more of the tip 910, telescoping sections 920a-i, or base 930 as can be accommodated. Moreover, unlike the electrodes depicted in FIGS. 2-4, the electrodes (912, 922a-i, 932) depicted in FIGS. 9A-B are longitudinally-spaced apart.

While the embodiments disclosed in the figures depict the telescoping sections as having a substantially circular cross-sectional dimension, it is understood that the telescoping sections may be configured in any number of geometric shapes (e.g., oval, rectangular, etc.) so long as the telescoping sections are capable being actuated between a nested or retracted configuration and an extended or deployed configuration.

It is to be understood that the detailed description and specific examples, while indicating embodiments of the present invention, are given by way of illustration and not limitation. Many changes and modifications within the scope of the present invention may be made without departing from the spirit thereof, and the invention includes all such modifications.

What is claimed is:

1. An elongate electrode assembly for a cochlear implant having a proximal end and a distal end, said elongate electrode assembly comprising:
   a base at the proximal end;
   a tip at the distal end;
   one or more telescoping sections between the base and the tip; and
   a plurality of electrodes disposed on any one or more of the base, tip and telescoping sections;
   wherein adjacent telescoping sections are slidably engaged with one another and movable between a retracted configuration and an expanded configuration.

2. The elongate electrode assembly of claim 1, wherein in the retracted configuration, the tip and the telescoping sections nest at least partially within the base.

3. The elongate electrode assembly of claim 2, wherein in the retracted configuration, the elongate electrode assembly is substantially straight.

4. The elongate electrode assembly of claim 1, wherein the telescoping sections are biased toward a first configuration in the expanded configuration, and wherein the first configuration is adapted to fit inside a patient's cochlea.

5. The elongate electrode assembly of claim 1, wherein the base and the telescoping sections define a lumen extending through the base and the telescoping sections when the elongate electrode assembly is in the expanded configuration.

6. The elongate electrode assembly of claim 5, wherein at least one telescoping section further comprise stops to prevent the telescoping section from uncoupling from another one of the telescoping sections.

7. The elongate electrode assembly of claim 5 wherein at least one of the telescoping sections further comprises at least one mating locking structure configured to prevent rotation of the telescoping section relative to another one of the telescoping sections.

8. A cochlear electrode assembly kit, comprising:
an elongate electrode assembly for a cochlear implant having a proximal end and a distal end, the elongate electrode assembly comprising:
a base at the proximal end;
a tip at the distal end;
one or more telescoping sections between the base and the tip; and
a plurality of electrodes disposed on any one or more of the base, tip and telescoping sections;
wherein adjacent telescoping sections are slidably engaged with one another and movable between a retracted configuration and an expanded configuration; and
wherein the plurality of telescoping sections and the tip define a lumen; and
a stylet configured to fit into the lumen and extend substantially through the telescoping sections to deploy the elongate electrode assembly from the retracted configuration to the expanded configuration.

9. The kit of claim 8, wherein the stylet has a pre-curved configuration that during deployment urges the electrode assembly to assume a shape substantially corresponding to a wall of a patient's cochlea.

10. The kit of claim 9, wherein in the retracted configuration, the elongate electrode assembly is substantially straight.

11. The kit of claim 8, wherein in the retracted configuration, the tip and the telescoping sections nest at least partially within the base.

12. The kit of claim 8, wherein the telescoping sections are biased toward a first configuration in the expanded configuration, and wherein the first configuration is adapted to fit inside a patient's cochlea.

13. The kit of claim 8, wherein the base and the telescoping sections define a lumen extending through the base and the telescoping sections when the elongate electrode assembly is in the expanded configuration.

14. The kit of claim 13, wherein at least one telescoping section further comprise stops to prevent the telescoping section from uncoupling from another one of the telescoping sections.

15. The kit of claim 13, wherein at least one of the telescoping sections further comprises at least one mating locking structure configured to prevent rotation of the telescoping section relative to another one of the telescoping sections.

16. A method of manufacturing a telescoping cochlear electrode assembly for implantation into the cochlear of a patient as part of a cochlear implant system comprising:
providing a plurality of sheets, the sheets each configured to accommodate one or more electrodes;
forming a plurality of tubular structures from the plurality of sheets, wherein the tubular structures have increasing cross-sectional dimensions and are configured to nest within larger ones of the tubular structures; and
coupling the tubular structures in order of cross-sectional dimensions such that the tubular structures may be slidably actuated between a nested configuration and an expanded configuration.

17. A method for implantation of a telescoping cochlear electrode assembly, the method comprising:
obtaining an elongate electrode assembly according to claim 1;
inserting the electrode assembly in its retracted configuration into a base of a patient's cochlea; and
expanding the electrode assembly to the expanded configuration.

18. The method of claim 17, wherein the base and the telescoping sections define a lumen extending through the base and the telescoping sections when the elongate electrode assembly is in the expanded configuration, and wherein expanding the electrode assembly comprises:
inserting a stylet into the lumen; and
expanding the telescoping sections to expand the electrode assembly to its expanded configuration using the stylet.

19. The method of claim 18, wherein at least one telescoping section further comprise stops to prevent the telescoping section from uncoupling from another one of the telescoping sections, and wherein expanding the telescoping sections comprises:
expanding the at least one telescoping section until the stop of the at least one telescoping section abuts a stop of the another one of the telescoping sections.

20. The method of claim 18, wherein in the retracted configuration, the tip and the telescoping sections nest at least partially within the base, and wherein expanding the telescoping sections comprises:
first expanding the tip of the electrode assembly to a deployed state followed by expanding each subsequent nested telescoping section of the electrode assembly.

21. The method of claim 18, wherein in the retracted configuration, the tip and the telescoping sections nest at least partially within the base, and wherein expanding the telescoping sections comprises:
expanding the tip and nested telescoping sections such that tip and the telescoping sections are simultaneously expanded to a deployed state.

* * * * *